United States Patent [19]

Ashtiani et al.

[11] Patent Number: 4,936,305

[45] Date of Patent: Jun. 26, 1990

[54] SHIELDED MAGNETIC ASSEMBLY FOR USE WITH A HEARING AID

[75] Inventors: Cyrus N. Ashtiani; Zoltan J. Cendes, both of Pittsburgh, Pa.

[73] Assignee: Richards Medical Company, Memphis, Tenn.

[21] Appl. No.: 221,932

[22] Filed: Jul. 20, 1988

[51] Int. Cl.[5] .................................................. A61N 1/00

[52] U.S. Cl. .............................. 128/420.6; 128/420.5; 600/25; 600/27; 600/12; 381/68

[58] Field of Search ............. 128/420.5, 420.6, 419 R, 128/784; 381/68; 600/25, 27, 12, 13; 335/301

[56] References Cited

U.S. PATENT DOCUMENTS

| | | | |
|---|---|---|---|
| 3,764,748 | 10/1973 | Branch et al. | 600/25 |
| 3,870,832 | 4/1975 | Frederickson | 128/420.6 |
| 4,606,329 | 8/1986 | Hough | 128/421 |
| 4,628,907 | 12/1986 | Epley | 600/25 |
| 4,776,322 | 10/1988 | Hough et al. | 128/420.6 |
| 4,817,607 | 4/1989 | Tatge | 128/419 R |

OTHER PUBLICATIONS

R. Goode and T. Glattke, *Audition via Electromagnetic Induction,* Arch Otolaryngol, Jul., 1973, pp. 23-26.

R. Goode, *An Implantable Hearing Aid,* Tr. Am. Acad. Opth. & Otol., Jan.-Feb., 1970, pp. 128-139.

J. Vernon, T. Mahoney and A. Schlevning II, *Implantable Hearing Aids,* pp. 249-268.

J. Fredrickson, D. Tomlinson, E. Davis and L. Odkvist, *Evaluation of an Electromagnetic Implantable Hearing Aid,* Canadian Journal of Otolaryngology, vol. 2, No. 1, 1973, pp. 53-62.

*Primary Examiner*—Francis Jaworski
*Assistant Examiner*—George Manuel
*Attorney, Agent, or Firm*—Pravel, Gambrell, Hewitt, Kimball & Krieger

[57] ABSTRACT

A shielded magnetic assembly for use in a magnetic hearing aid is described. The shielded assembly uses a disc-shaped magnet with a high permeability, low coercivity material placed on the face of the magnet away from the air gap. Preferably, the shielding material also covers portions of the edge of the magnet to form a cap. The shielding focuses the magnet's energy into the air gap to improve coupling and reduce interference from external magnetic fields.

16 Claims, 11 Drawing Sheets

SHIELDED MAGNETIC ASSEMBLY FOR USE WITH A HEARING AID

BACKGROUND OF THE INVENTION

1. Field of the Invention

The present invention relates to magnet structures and more particularly to magnet structures for use with magnetically coupled hearing aids.

2. Description of the Prior Art

Conventional hearing aids utilize detection, amplification and retransmission of the acoustic waves forming sound. Because of a number of well known problems with conventional hearing aids, magnetically coupled hearing aids were investigated. In a magnetically coupled hearing aid a magnet or magnetic material is placed in the middle ear so that any movement of the magnet structure is perceived as sound by the wearer. The hearing aid includes a coil used to develop a magnetic field which is coupled to the magnetic field produced by the magnetic material. The coil magnetic field is varied based on the received sound waves, with the coupling between the two fields causing the magnetic material to vibrate in sympathy. This motion of the magnetic material then vibrates the connected portion of the middle ear and sound is perceived by the wearer.

Because these magnetic hearing aids are electrically powered, generally by very small batteries, overall efficiency is critical with the highest possible efficiency being desirable. The increased power consumption that is necessitated if the electrical circuitry utilizes too much power itself or if the coupling between the magnetic fields is poor may reduce efficiency of the hearing aid, and therefore the battery life, to unacceptable limits. Because of the state of current electronics, the most promising area for improvement is the coupling of the magnetic fields.

While increasing the size and therefore field strength of the implanted magnetic material is a possibility to improve magnetic field coupling, the larger amount of magnetic material is also increasingly vulnerable to external magnetic fields. For example, if the user is too close to the external magnetic field from an electrical transformer, a 60 Hz hum may be developed by the coupling of the magnetic material magnetic field and the transformer magnetic field. This is a drawback to simply increasing the size of the magnetic material and is an effect which is desirable to limit.

The coupling could be increased by increasing the strength of the magnetic field output by the hearing aid coil. One way to increase this field is to increase the current in the coil, thereby increasing the ampere-turns value. This increase is practical only within given limits because the increase in current directly affects battery life. Increasing the number of turns is also possible, but again has practical limitations. Because of the limited volume that can be occupied by the coil, especially if the coil is located in the ear canal, the number of turns can only be increased by reducing the size of the wire forming the coil. However, as this wire size is reduced, its unit resistance, and therefore overall coil resistance, increases. Because the amplifier driving the coil is customarily a voltage source, it is sensitive to this output load and the current provided to the coil can reduce as the resistance increases. Therefore, there are only limited gains to be obtained by changing the coil current or number of turns. Gains must be developed in a manner other than simply increasing ampere-turns value.

The coil could be placed closer to the magnetic material, but given the size of the hearing aid components and the vulnerability of the middle ear, certain effective minimum spacings are necessary, particularly if the extended surgery that may be necessary for very close implantation is not desirable or possible. Additionally, it is desirable that as much of the hearing aid as possible is easily removable, to limit surgical problems and to ease repair and replacement of the hearing aid and its battery. This removability, when coupled with the physical sizes of the hearing aid components, limits the attainable distance between the coil and magnetic material.

SUMMARY OF THE INVENTION

A magnetic assembly according to the present invention utilizes a magnetic material and a shielding cap. The shielding cap is a highly permeable, low coercivity material which is located on at least the side of the magnetic material away from the air gap between the coil and the magnetic material. The shielding cap confines the energy stored in the magnetic material's magnetic field to the region or air gap between the coil and the magnetic material. This confining or focusing of the energy results in improved coupling between the two magnetic fields, with the concomitant increase in the hearing aid's efficiency. The shielding cap has the added benefit of reducing the interaction between the magnetic material and external magnetic fields.

The magnetic material is preferably disc-shaped, having a thickness less than the effective width or diameter. Preferably the magnetic material is a high energy material such as samarium cobalt or neodymium-iron.

The shielding cap is shaped to mate with the magnetic material and cover at least one face, with the shielding cap preferably extending over the edges of the disc, so that over one-half, effectively one magnetic pole, of the magnetic material is surrounded by the shielding cap. The shielding cap is formed of a high permeability, low coercivity material, such as permalloy or mumetal.

The magnetic material and the shielding cap preferably have a uniform thickness, but may have a thickness varying with the distance from the longitudinal axis of the assembly.

BRIEF DESCRIPTION OF THE DRAWINGS

A better understanding of the invention can be obtained when the following detailed description of exemplary embodiments is considered in conjunction with the following drawings, in which.

DETAILED DESCRIPTION OF EXEMPLARY EMBODIMENTS

An uncapped magnet U (FIG. 1) has a magnetic field $F_u$ which is symmetric or uniform about the faces 10 and 12 of the magnet U when the magnetic poles are aligned with the faces 10 and 12 of the magnet U. The representations of the magnets and their respective magnetic fields in the figures are shown as two dimensional for simplicity and ease of explanation, but it is understood that the shapes of the magnets and fields are three dimensional, generally developed by revolving the illustrated portions about an axis for cylindrical embodiments. The energy stored in this uniform magnetic field $F_u$ can be considered as being stored in the volume enclosed by the representative lines of flux. As a result, the energy density is high near the field source, the magnet U, and diminishes with the distance from the field source.

In a magnetically coupled hearing aid, a coil C (FIG. 2) produces a magnetic field $F_c$. In the hearing aid a microphone receives the acoustic sound waves and converts them into an electrical signal. This signal is filtered if desired and amplified. The amplified signal is applied to the coil C which produces the magnetic field $F_c$. The magnetic field $F_c$ varies with the frequency and amplitude of the sound waves received by the hearing aid, as explained in U.S. Pat. application, Ser. No. 837,708, filed Mar. 7, 1986 issued as U.S. Pat. No. 4,800,884 on Jan. 31, 1989, and owned by the same entity that owns the subject application, the disclosure of which is hereby incorporated by reference as though fully contained herein, and as described in the article by R. Goode and T. Glattke, "Audition Via Electromagnetic Induction," *Arch Otolaryngol*, July 1978 at pages 23–26.

Figure 2:
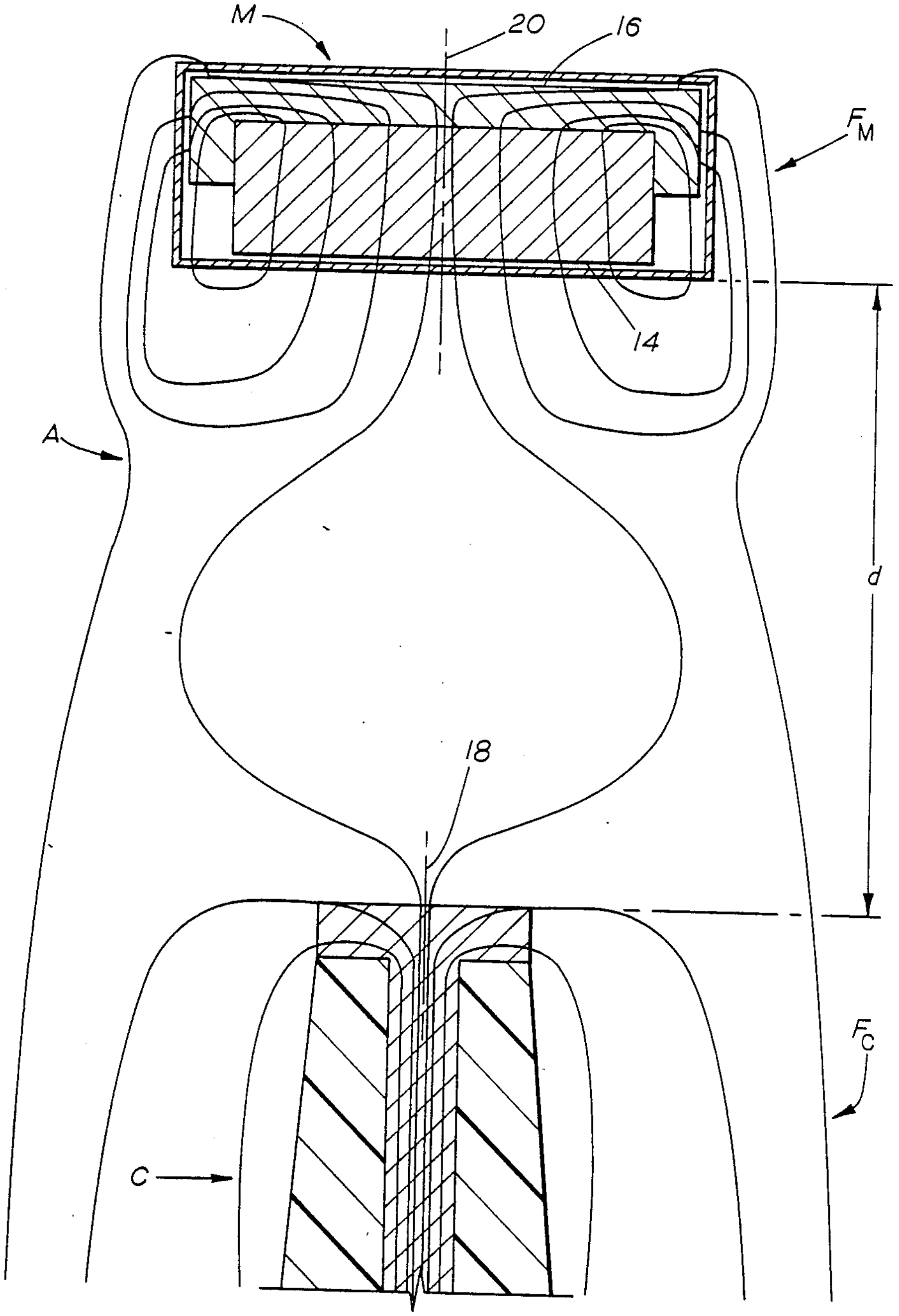
FIG. 2 is a schematic view of a shielded magnetic assembly of the present invention along with a magnetic hearing aid coil and representations of their respective flux lines.

The coil field $F_c$ interacts with the magnetic field $F_m$ produced by a magnet M. The magnetic field $F_m$ is a constant field because the magnet M has a fixed strength. When the coil field $F_c$ varies, the coupling or interaction between the coil field $F_c$ and the magnet field $F_m$ causes the magnet M to vibrate at the frequency of the coil field $F_c$. This coupling is shown in FIG. 2 where the fields $F_c$ and $F_m$ are of opposite or attractive polarity, so that the flux lines appear to merge, because the magnetic circuit is being formed between the magnet M and the coil C. When the fields $F_c$ and $F_m$ are of like or repulsive polarity in the air gap, the respective flux lines are closed loops, indicating that two magnetic circuits are present.

The amplitude of the vibration of the magnet M varies depending on the quality of the coupling of the two fields $F_c$ and $F_m$ and the mass of the magnet M. The quality of the coupling is based on the air gap distance d and the strength or interacting energy of the two fields $F_c$ and $F_m$. If the air gap distance d is reduced or the strength or interacting energy of one of the fields $F_c$ or $F_m$ is increased, the coupling improves and the vibrational amplitude of the magnet M increases. Because a given amplitude of magnet M movement is necessary to produce a perceived sound level, improving the coupling increases the perceived sound level. If the energy consumption of the hearing aid is not increased in improving the coupling, the efficiency of the hearing aid is increased and battery life is extended.

The magnet M has one face 14 substantially facing the coil C and one face 16 substantially facing away from the coil C with the magnetic poles generally aligned with these faces 14 and 16. The axis 20 of the magnet M is generally aligned with the axis 18 of the coil C in the embodiment illustrated in FIG. 2.

Figure 1:
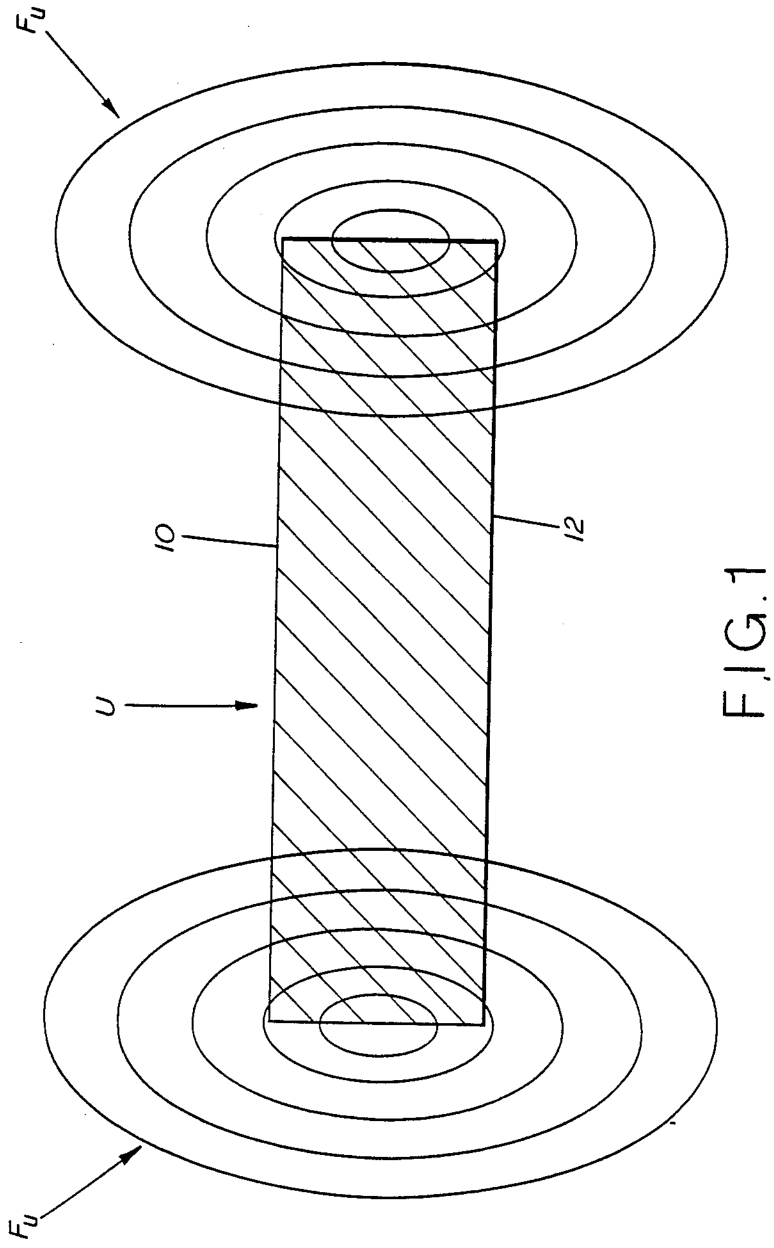
FIG. 1 (PRIOR ART)
FIG. 1 is a schematic view of a magnet according to the prior art and its representative flux lines.

As previously discussed, changing the strength of the coil field $F_c$ is not preferable and the air gap distance d cannot be easily changed, so the magnet field $F_m$ or its coupling with the coil field $F_c$ must be improved. As shown in FIG. 1, the magnetic field $F_u$ of the uncoated magnet U is uniform about the two faces 10 and 12 of the magnet U. Thus an appreciable portion of the energy stored in the field $F_u$ is not utilized in the coupling of the uncoated magnet U and the coil C. It is desirable that more of the energy be focused into the air gap A, so that the useful energy developed in the magnet field $F_m$ is increased.

The shielded magnet assembly S (FIG. 3), which is similar to the magnet M of FIG. 2, with the letter S generally referring to a shielded magnet assembly according to the present invention and the numeral referring to a particular embodiment, focuses or directs more of the energy contained in its magnetic field $F_{s1}$ into the air gap A than an uncoated magnet U of equivalent strength. The shielded assembly $S_1$ is comprised of two pieces, a magnet 22 and a shielding cap 24. The magnet 22 is preferably cylindrical (FIG. 4) and relatively thin, so that the magnet 22 has a radius r and a thickness t, with the thickness t preferably being less than twice the radius r. Of course, the magnet 22 can have other shapes as desired, such as hexagonal or square, or other shapes as are apparent to those skilled in the art. The magnet 22 is preferably formed of high energy magnetic materials, such as samarium cobalt, neodymium-iron or other similar materials, to reduce the size and mass of the magnet 22 needed to develop a given magnetic field $F_{s1}$. The magnet 22 is formed using conventional techniques.

The shielding cap 24 is shaped to mate with the magnet 22. The cap 24 contains a recess 26 into which the magnet 22 fits snugly. Preferably the air gaps between the cap 24 and the magnet 22 are kept to a minimum to increase the magnet field focusing property of the assembly S . The recess 26 has a depth of approximately one-half the magnet thickness t so that effectively one pole of the magnet 22 is shielded, limiting the magnetic flux which can form a circuit without traversing the shielding cap 24. The shielding cap 24 is preferably formed of a high permeability and low coercivity material, for example, permalloy or mumetal. The material can be annealed to increase the relative permeability of the material, but satisfactory results are had when the material is not annealed. The shielding cap 24 is preferably machined from either cylindrical stock or from stock cast to approximate the finished shape to keep any differences between the shape of the recess 26 and the magnet 22 to a minimum.

Because the permeability of the shielding cap 24 is so high relative to air, the flux lines representing the magnetic field $F_{s1}$ of the magnet 22 are distorted from the uniform pattern of the unshielded magnet U. A series magnetic circuit is formed from one face or pole 28 of the magnet 22 to the other face 30, with the circuit elements being the shielding cap 24 and the air in the volume where the circuit is completed. In a series magnetic circuit the energy is primarily stored in the least permeable portions of the circuit. Therefore the energy in the shielded field $F_{s1}$ is contained primarily in the air gap A, resulting in improved coupling between the coil field $F_c$ and the shielded field $F_{s1}$ over the unshielded field $F_u$ because of the increased energy in the air gap A for the magnetic field $F_{s1}$, which improves the magnetic coupling.

Various tests were performed to compare the shielded assembly $S_1$ with the uncapped magnet U. A magnet having an approximate diameter of 0.1 inches and an approximate thickness of 0.03 inches, formed of samarium cobalt, and weighing approximately 32 mg was used in the tests. A shielding cap 24 formed of cold-rolled or unannealed permalloy, having an approximate thickness of 0.01 inches, and weighing approximately 25 mg was attached to the magnet U to form the shielded assembly $S_1$ tested. An air gap of approximately 0.125 inches was present between the magnet and a test coil formed by placing approximately 2500 turns of 48 gauge x 3 Litz wire over a 0.025 inch diameter permalloy core. Three different tests were performed, two with 750 μA of current in the coil and one with 500 μA of current in the coil.

| Test Frequency (Hz) | Uncapped Magnet U (dBSPL) | Shielded Assembly $S_1$ (dBSPL) | Improvement with Shielding (dBSPL) |
|---|---|---|---|
| | TEST 1<br>Effective Sound Pressure Levels of Shielded and Unshielded Magnets<br>Coil Current of 750 μA | | |
| 125 | 102.1 | 110.0 | 8.0 |
| 250 | 103.5 | 113.2 | 9.7 |
| 500 | 106.2 | 114.4 | 8.2 |
| 750 | 103.4 | 116.4 | 11.0 |
| 1000 | 103.0 | 113.5 | 10.5 |
| 1500 | 103.2 | 116.2 | 11.0 |
| 2000 | 106.2 | 119.0 | 12.8 |
| 3000 | 109.5 | 121.0 | 11.5 |
| 4000 | 108.4 | 115.5 | 7.1 |
| 5000 | 102.1 | 112.4 | 10.3 |
| 6000 | 95.5 | 103.7 | 8.2 |
| 7000 | 93.2 | 108.6 | 15.6 |
| 8000 | 95.5 | 103.5 | 8.0 |
| | TEST 2<br>Effective Sound Pressure Levels of Shielded and Unshielded Magnets<br>Coil Current of 750 μA | | |
| 125 | 98.3 | 106.4 | 8.5 |
| 250 | 100.8 | 106.4 | 5.6 |
| 500 | 100.5 | 105.9 | 5.4 |
| 750 | 99.6 | 108.0 | 8.4 |
| 1000 | 98.6 | 108.0 | 9.4 |
| 1500 | 100.7 | 106.4 | 5.7 |
| 2000 | 99.8 | 104.4 | 4.6 |
| 3000 | 106.5 | 106.7 | 0.2 |
| 4000 | 98.2 | 102.8 | 4.6 |
| 5000 | 96.1 | 87.2 | −8.9 |
| 6000 | 83.1 | 99.7 | 16.6 |
| 7000 | 82.7 | 93.7 | 11.0 |
| 8000 | 83.1 | 86.2 | ·3.1 |
| | TEST 3<br>Effective Sound Pressure Levels of Shielded and Unshielded Magnets<br>Coil Current of 500 μA | | |
| 125 | 96.5 | 103.8 | 7.3 |
| 250 | 98.0 | 102.3 | 4.7 |
| 500 | 97.5 | 97.5 | 0.0 |
| 750 | 97.6 | 98.1 | 0.5 |
| 1000 | 96.8 | 99.6 | 2.8 |
| 1500 | 97.4 | 95.5 | −1.9 |
| 2000 | 97.0 | 99.9 | 2.9 |
| 3000 | 100.9 | 101.1 | 0.2 |
| 4000 | 96.4 | 99.9 | 3.5 |

-continued

| Test Frequency (Hz) | Uncapped Magnet U (dBSPL) | Shielded Assembly $S_1$ (dBSPL) | Improvement with Shielding (dBSPL) |
|---|---|---|---|
| | TEST 1<br>Effective Sound Pressure Levels of Shielded and Unshielded Magnets<br>Coil Current of 750 μA | | |
| 5000 | 92.7 | 98.4 | 5.7 |
| 6000 | 82.0 | 97.2 | 15.2 |
| 7000 | 80.0 | 91.5 | 11.5 |
| 8000 | 81.5 | 85.4 | 3.9 |

As shown, the shielded assembly $S_1$ has a greater effective output level, particularly at the higher frequencies between 5000 and 8000 Hz, than an unshielded magnet U given equal magnet sizes and magnet energies.

A fourth test was performed with an uncapped magnet U of the same material and diameter, but having an increased thickness to approximately 0.05 inches, so that the magnet U weighed approximately 57 mg, the same as the shielded assembly $S_1$, under test.

TEST 4
Effective Sound Pressure Levels of Shielded and Unshielded Magnets
Coil Current of 750 μA

| Test Frequency (Hz) | 57 mg Uncapped Magnet U (dBSPL) | Shielded Assembly $S_1$ (dBSPL) | Improvement with Shielding (dBSPL) |
|---|---|---|---|
| 125 | 97.4 | 99.1 | 1.7 |
| 250 | 97.7 | 96.3 | −1.4 |
| 500 | 95.2 | 96.5 | 1.3 |
| 750 | 94.8 | 95.2 | 0.4 |
| 1000 | 94.7 | 94.6 | −0.1 |
| 1500 | 95.8 | 94.4 | −1.4 |
| 2000 | 93.0 | 94.3 | 1.3 |
| 3000 | 86.6 | 88.7 | 2.1 |
| 4000 | 79.7 | 86.4 | 6.7 |
| 5000 | 65.8 | 77.6 | 11.8 |
| 6000 | 65.0 | 67.4 | 2.4 |
| 7000 | 54.9 | 60.4 | 5.5 |
| 8000 | 63.1 | 62.3 | −0.8 |

The shielded assembly $S_1$ does provide improved output characteristics at higher frequencies when compared with an uncapped magnet U having the same weight as the shielded assembly $S_1$. However, the larger unshielded magnet U is vulnerable to interference developed by the presence of external magnetic fields. The external fields can be produced by transformers used in electronic equipment. The external fields couple with the magnetic field of the magnet and cause a low frequency interference to be heard by the wearer.

The focusing of the magnetic field $F_{s1}$ in the air gap A and the resultant decrease in the field $F_{s1}$ in other positions reduces the interference caused by external magnetic fields. Less energy exists in positions not coupled with the coil C. As a result, there is less energy to easily couple with external fields produced by transformers and the like, and any external coupling occurring in the air gap region must overcome the signal or field of the coil C. Therefore the shielded assembly $S_1$ has a reduced amount of external field pickup. Tests were performed using the unshielded magnet U and the shielded magnet assembly $S_1$ of Test 4. When this assembly $S_1$ was placed near a power transformer, a vibration equivalent to a sound pressure level of 87.4 decibels was obtained. The uncapped magnet U in the same location produced a vibration equivalent to a sound pressure level of 109.9 decibels, or an increase of 22.5 decibels over the shielded assembly $S_1$.

The shielding cap 24 covers the edge of magnet 22 so that effectively one entire pole of the magnet 22 is covered and no paths exist which do not include the shielding cap 24 in the magnetic circuit. This improves the effectiveness of the magnetic field focus as compared to a second shielded assembly $S_2$ (FIG. 5), where a shielding disc 32 is provided instead of a shielding cap 24. The shielding disc 32 is substantially the same size and shape as the back face 28 of the magnet 22 and does not overlap the edges of the magnet 22. As a result, the disc 32 does not bend or focus the magnetic field $F_{s2}$ into the air gap A as much as the shielding cap 24 and the coupling between the magnetic fields of the disc shielded assembly $S_2$ and the coil C is less than the coupling between the magnetic fields of the capped magnet assembly $S_1$ and the coil C. However, the coupling of the fields $F_{s2}$ and $F_c$ is still an improvement over an unshielded magnet U. The disc 32 is preferably formed of similar material as the shielding cap 24.

Figure 3:
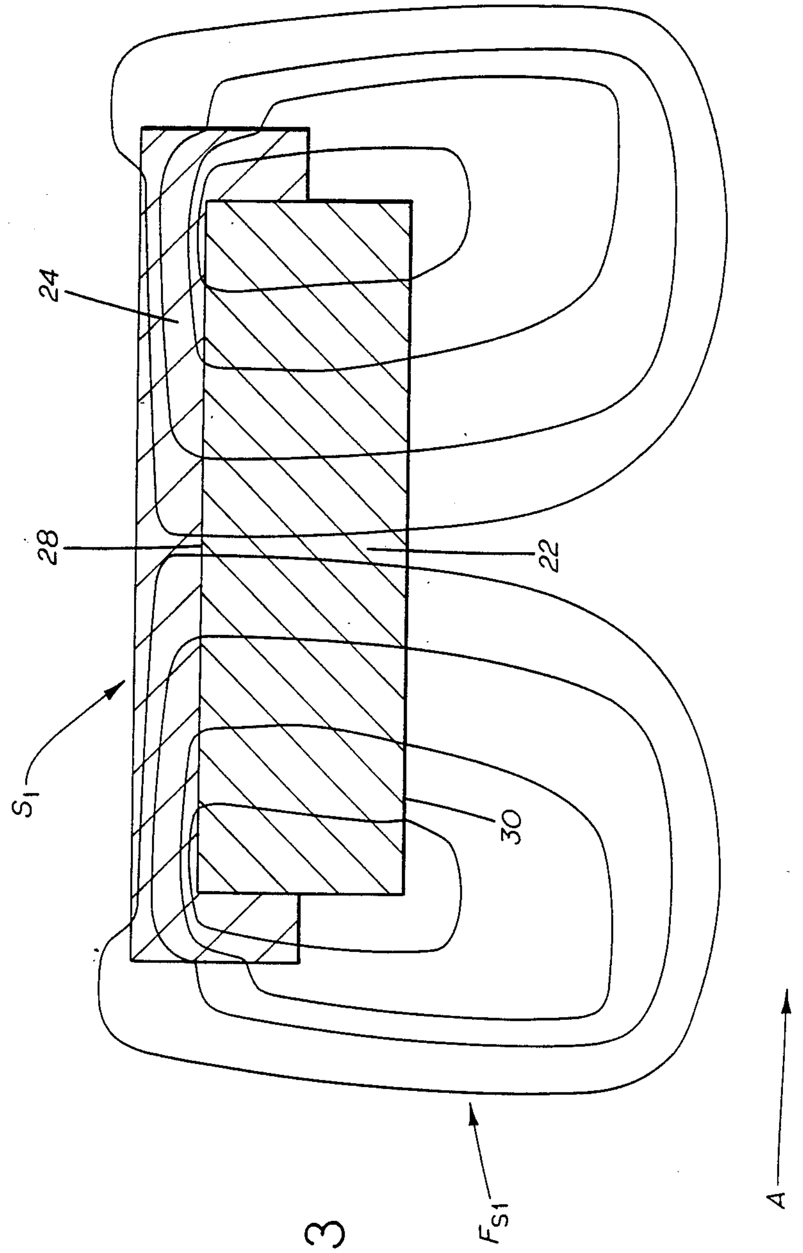
FIGS. 3, 5 and 6 are schematic views of shielded magnetic assemblies according to the present invention and representations of their respective flux lines.
Figure 4:
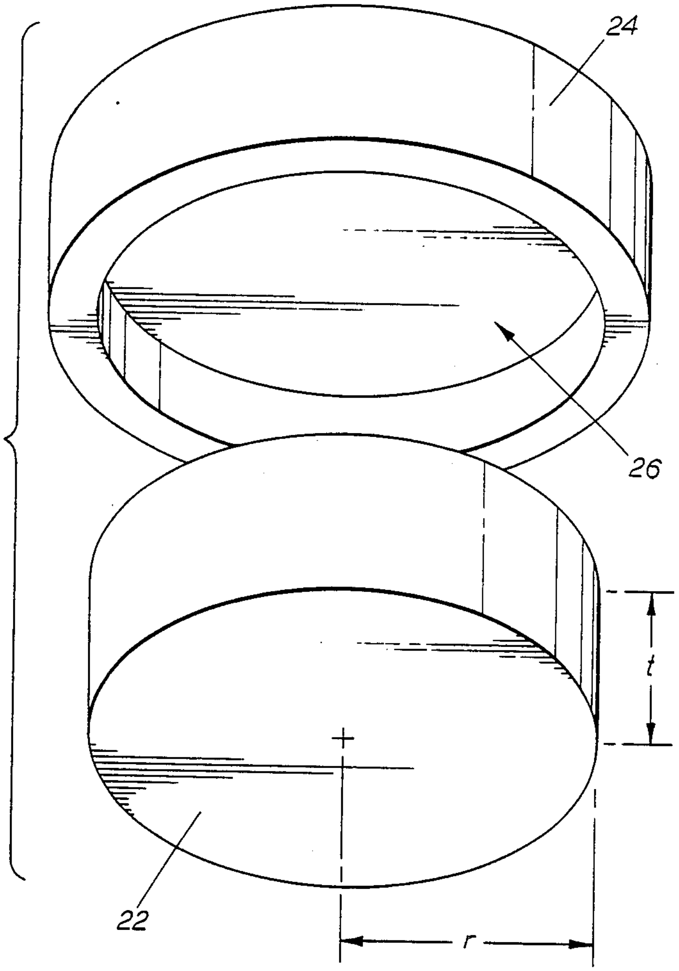
FIG. 4 is an exploded, perspective view of the shielded magnetic assembly of FIGS. 2 and 3.
Figure 5:
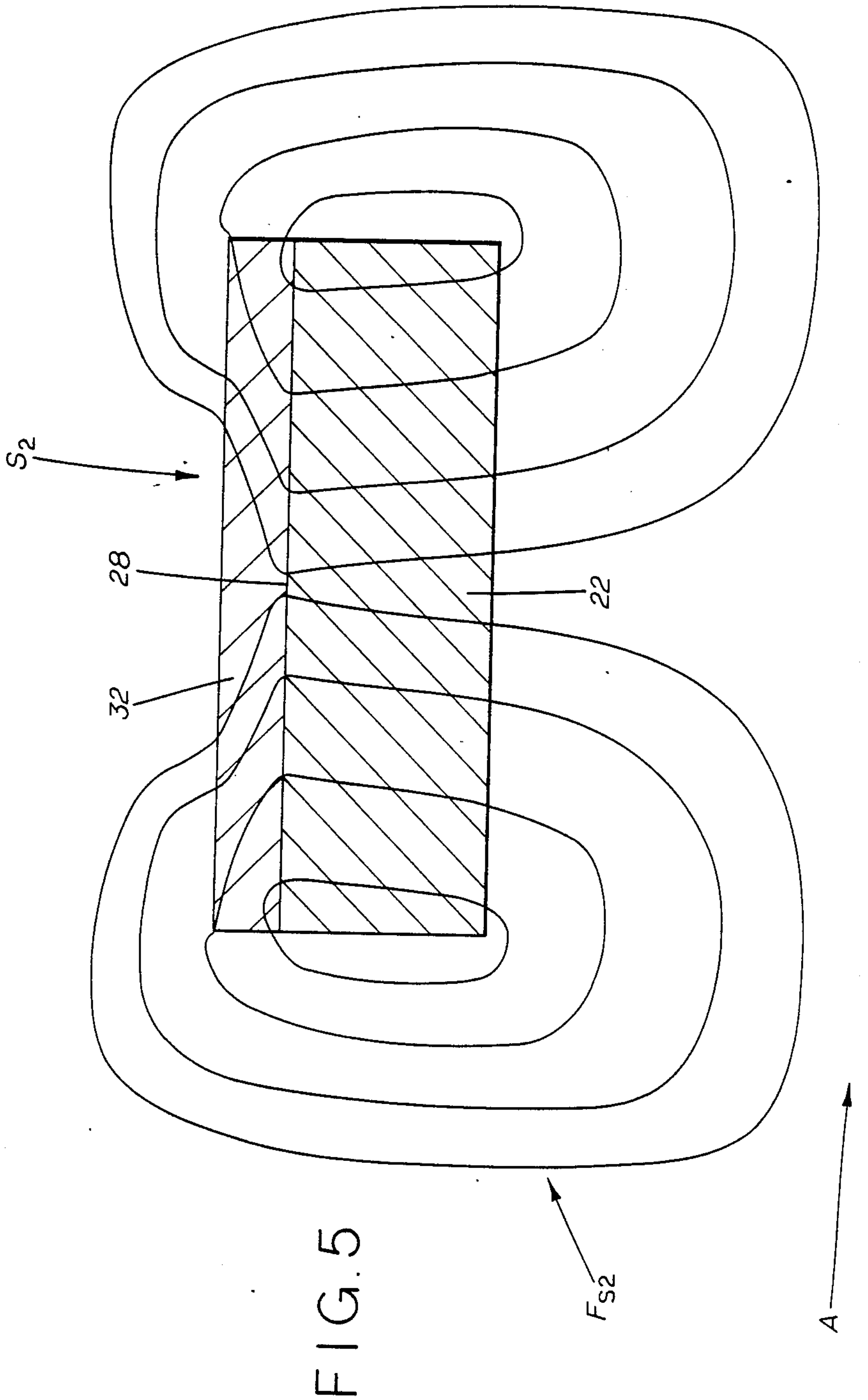
Figure 6:
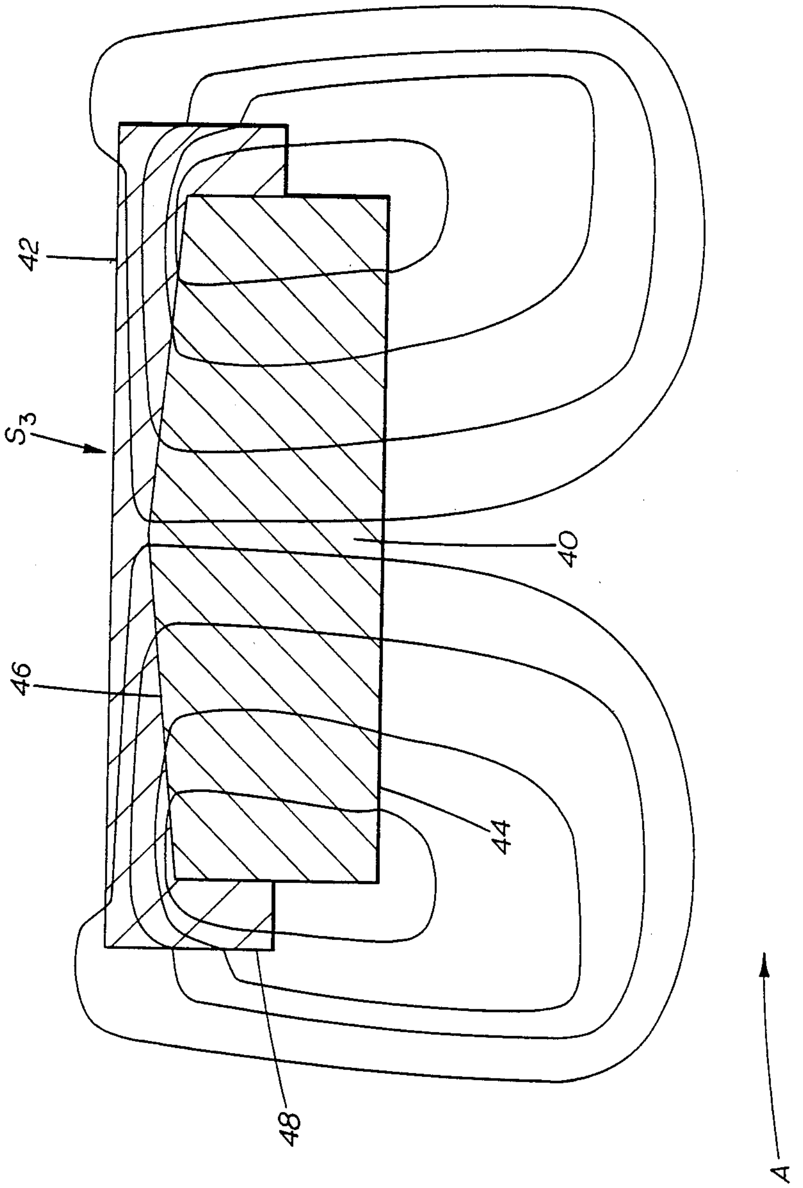

In the embodiments of the present invention disclosed in FIGS. 3 and 5, the shielding cap 24 and the disc 32 have a uniform thickness. In an alternate embodiment illustrated in FIG. 6, a magnetic assembly $S_3$ is provided having a magnet 40 and a shielding cap 42 with varying thicknesses. The magnet 40 is generally cylindrical, having a plane face 44 on the air gap A side and a conical face 46 away from the air gap A. The tapered shielding cap 42 is correspondingly thin at the central axis, and thickens to the edge of the magnet 40. The tapered cap 42 preferably has a lip 48 which covers portions of the edge of the magnet 40 to allow improved magnetic field focusing. Again, the magnet 40 is preferably formed of a high energy material and the tapered cap 42 is formed of a high permeability, low coercivity material.

Figure 7:
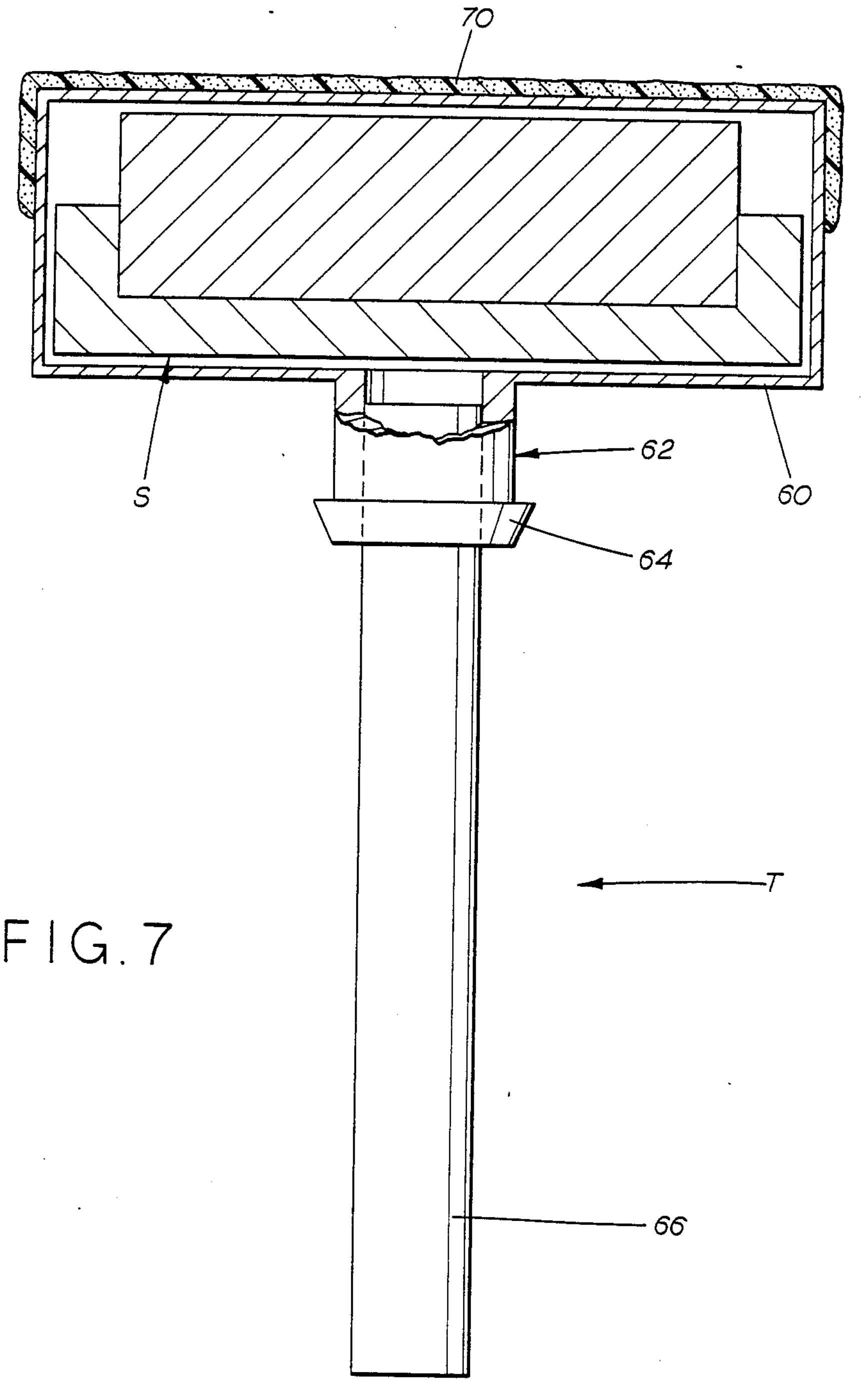
FIGS. 7 and 8 are side views in partial cross-section of prostheses including a shielded magnetic assembly according to the present invention.
Figure 7A:
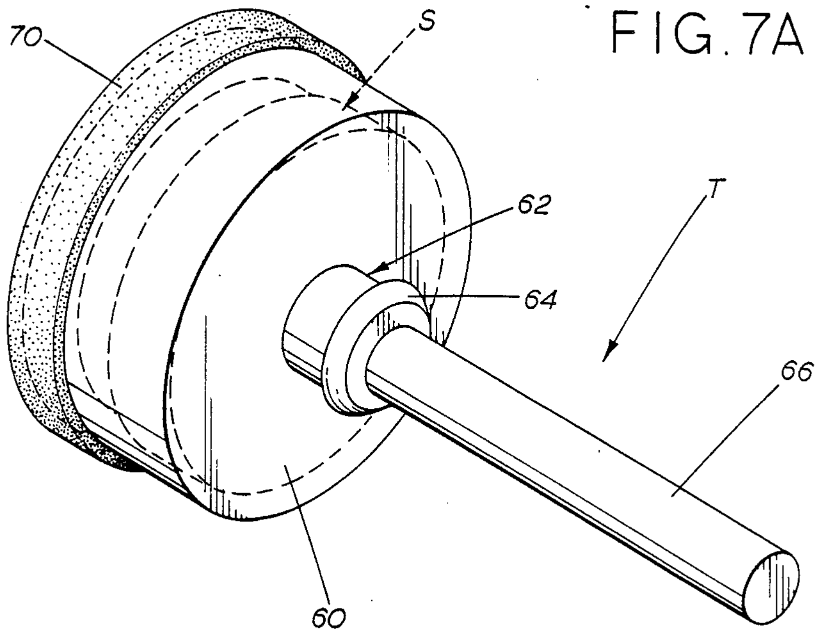
FIGS. 7A and 8A are perspective views of the prostheses of FIGS. 7 and 8, respectively.
Figure 8A:
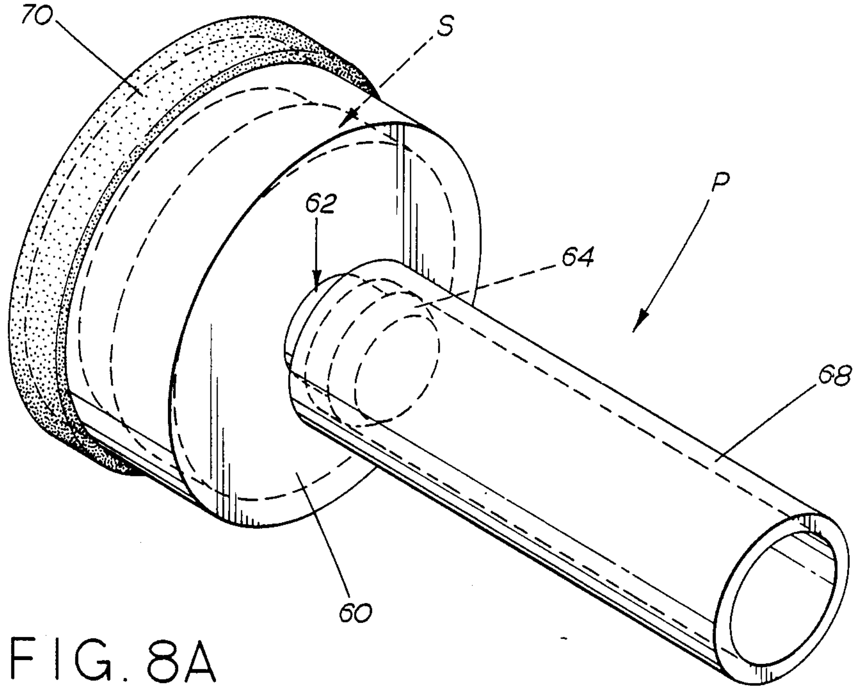
Figure 8:
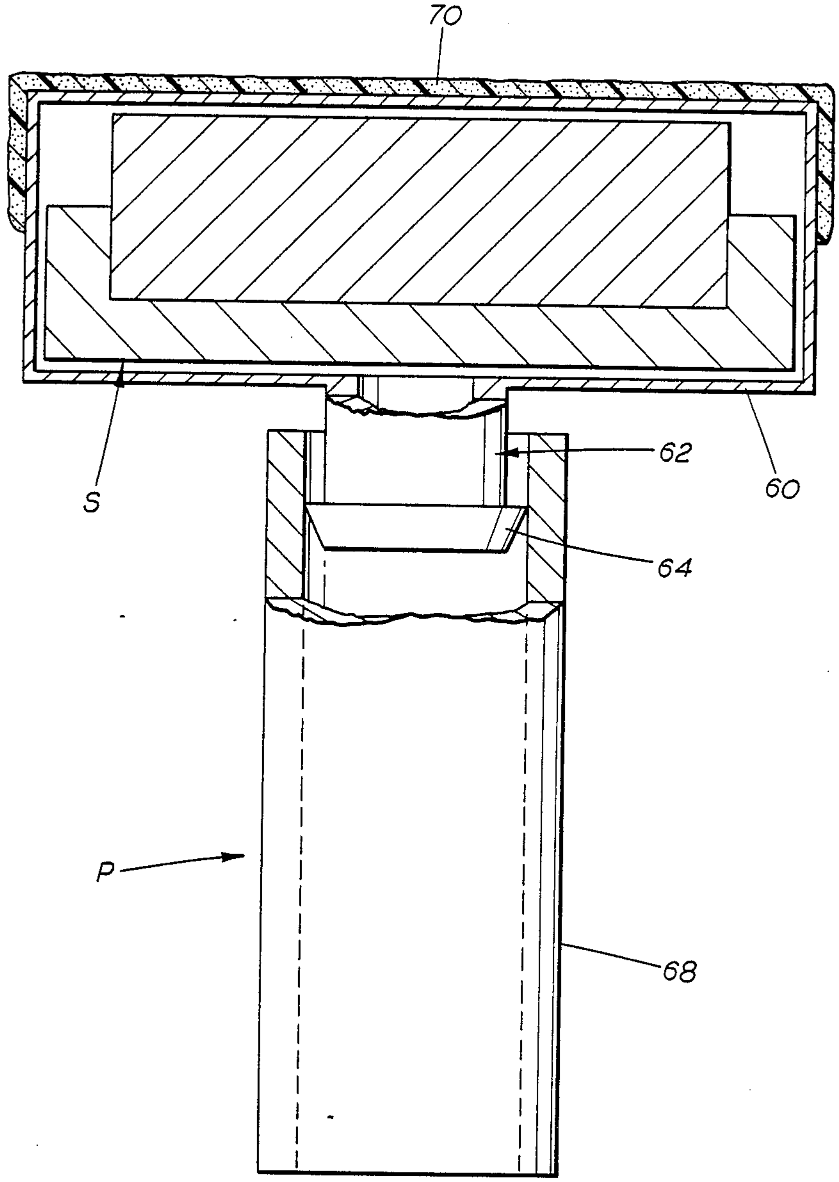

The shielded magnet assembly S can be placed in the ear in a number of ways. The magnet assembly S can be placed in a total ossicular replacement prosthesis T (FIGS. 7 and 7A) or a partial ossicular replacement prosthesis P (FIGS. 8 and 8A) according to the disclosure of U.S. Pat. application, Ser. No. 050,909, filed May 15, 1987, issued as U.S. Pat. No. 4,817,607 on Apr. 4, 1989, and owned by the same entity that owns the subject application, the disclosure of which is hereby incorporated by reference as though fully contained herein.

The shielded magnet assembly S is placed inside a biocompatible container 60. The container 60 is preferably formed of titanium, but can be formed of any suitable biocompatible material which has a relative magnetic permeability of approximately one and can seal the shielded magnet assembly S from the body. The container 60 includes a generally cylindrical mounting post 62 which is preferably hollow and has an outer surface including a tapered portion 64. When the container 60 is used in a total replacement prosthesis T, a shaft 66 is inserted into the hollow portion of the mounting post 62. When the container 60 is used in a partial replacement prosthesis P a hollow shaft 68 is used, with the hollow shaft 68 being installed over the mounting post 62, so that the tapered portion 64 grips the inside of the shaft 68.

The container 60 preferably has a porous biocompatible coating 70 over the portion of the container 60 which contacts the tympanic membrane. This porous coating 70 can be an appropriate polymer or hydroxyapatite, to allow positive connection to the tympanic membrane over time as tissue ingrowth occurs.

Figure 9:
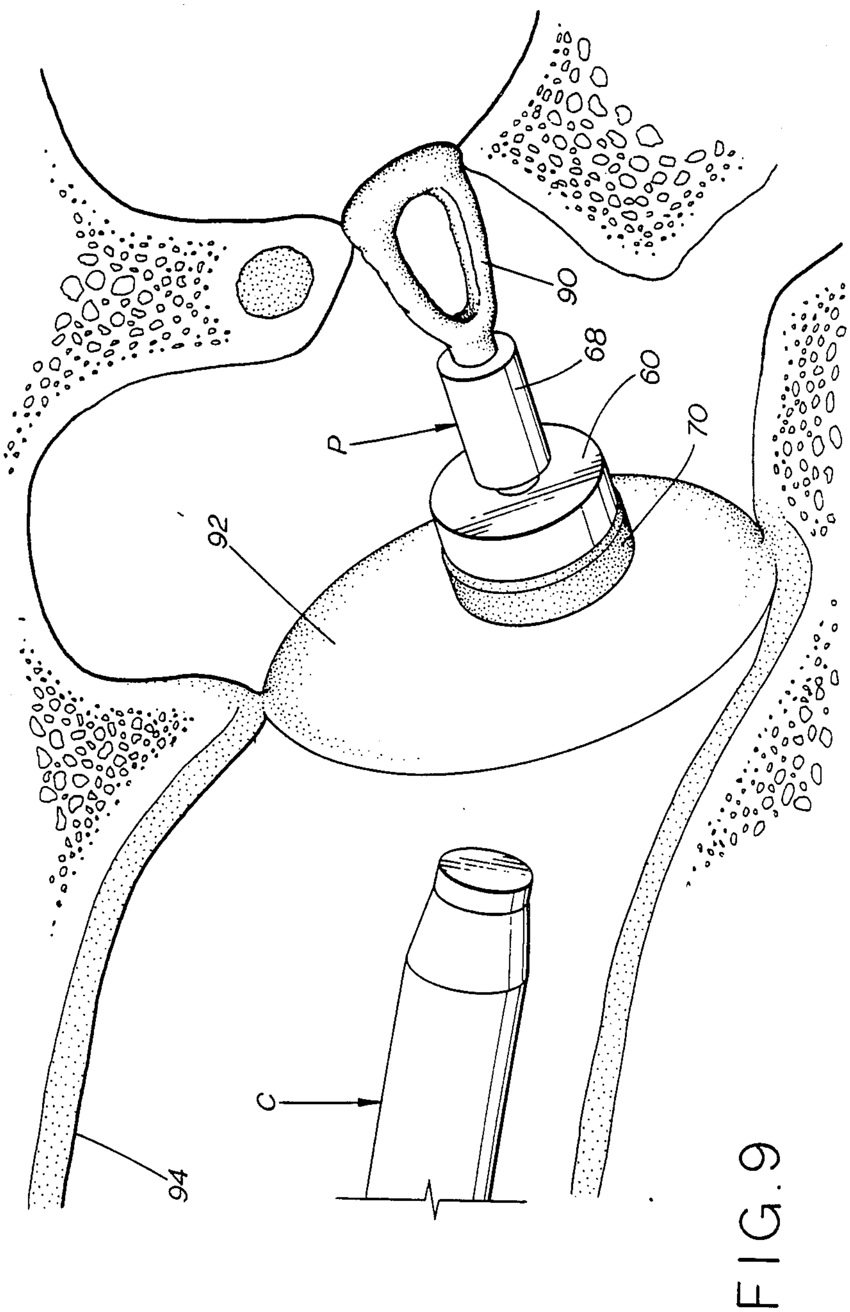
FIG. 9 is a representation showing the ear canal, the middle ear, a coil and the prosthesis of FIG. 8.

The partial prosthesis P is shown implanted in the middle ear in FIG. 9. The malleus and the incus have been removed as appropriate when using a partial ossicular replacement prosthesis. The partial prosthesis P contacts the tympanic membrane 92 and the stapes 90 to provide conduction of the received acoustic waves to the inner ear 94. The coil C of the hearing aid is shown placed in the ear canal 94, so that the magnetic fields of the coil C and the shielded assembly S in the partial prosthesis P can interact and provide movement to the stapes 90 to simulate sound. Therefore the partial prosthesis P allows both acoustic and magnetic energy to be transferred to the inner ear to be perceived as sound.

Figure 10:
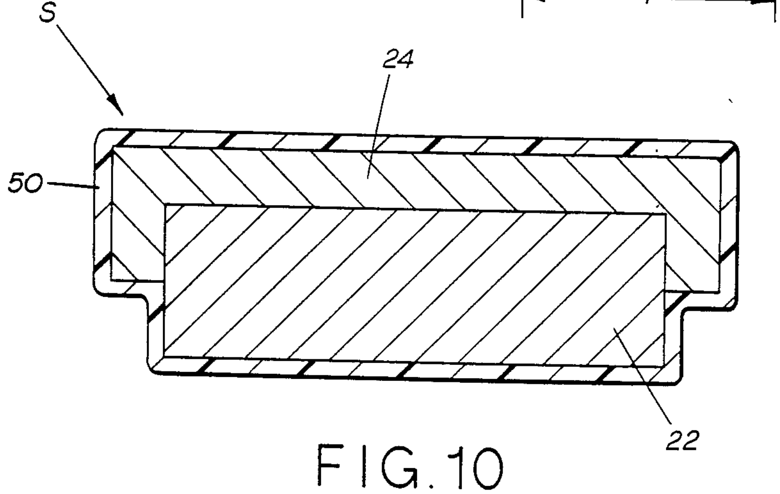
FIG. 10 is a cross-sectional view of a coated, shielded magnetic assembly according to the present invention.

As yet another alternative, the shielded assembly S can be directly implanted in an appropriate location in the middle ear. Such an assembly S may be directly biocompatibly coated 50 (FIG. 10) or may be placed in a biocompatible container (not shown) which has a further biocompatible coating. The magnet 20 and shielding cap 24 are coated by the biocompatible coating 50 to prevent corrosion or rejection when implanted and preferably to allow tissue ingrowth for positive attachment. The biocompatible coating 50 may be any satisfactory material, such as hydroxyapatite, biocompatible polymers, and other materials known to those skilled in the art.

The foregoing disclosure and description of the invention are illustrative and explanatory thereof, and various changes in the size, shape, materials, components, circuit elements, as well as in the details of the illustrated circuitry and construction may be made without departing from the spirit of the invention.

We claim:

1. A magnet assembly for implantation in an ear and for use with the magnetic field produced by the coil of a magnetically coupled hearing aid, for producing vibration of portions of the middle ear, the assembly comprising:

magnet means adapted to be spaced a fixed distance from the coil for forming an air gap, said magnet means including a front face adapted to face the air gap, a back face adapted to face away from the air gap, and a side face generally connecting said front and back faces; and shielding cap means connected to said magnet means for focusing the magnetic energy of said magnet means, said shielding cap means formed of material having a high relative magnetic permeability and having a size and shape to substantially conform to the size and shape of said back face of said magnet means.

2. The magnet assembly of claim 1, wherein said shielding cap means is further located adjacent the side face of said magnet means and has a size and shape to substantially conform to part of the thickness of said side face of said magnet means.

3. The magnet assembly of claim 1, wherein said magnet means front and back faces have an area substantially greater than the area of said side face and thus develop a central axis from the center of said front face to the center of said back face and said magnet means and said shielding cap means have a thickness varying with the distance from the central axis of the magnet means.

4. The magnet assembly of claim 3, wherein said shielding cap means is located adjacent said side face of said magnet means and has a size and shape to substantially conform to part of the thickness of said side face of said magnet means.

5. The magnet assembly of claim 1, wherein said shielding cap means consists essentially of permalloy.

6. The magnet assembly of claim 5, wherein said permalloy shielding cap means is annealed.

7. The magnet assembly of claim 1, wherein said shielding cap means consists essentially of mumetal.

8. The magnet assembly of claim 7, wherein said mumetal shielding cap is annealed.

9. A magnet induction hearing aid, comprising:

microphone means for producing an electrical signal in response to received sound waves;

amplifier means for amplifying said microphone means signal;

electrical power means for powering said amplifier means;

magnetic coil means driven by said amplifier means for producing a magnetic field indicative of the received sound waves; and magnet assembly means adapted to connect to a portion of the middle ear;

wherein said magnet assembly means is induced into movement by the magnetic field produced by said coil means such that said magnet assembly means produces movement of the middle ear indicative of the received sound waves; and wherein said magnet assembly means comprises:

magnet means adapted to be spaced a fixed distance from said magnetic coil means for forming an air gap, said magnet means including a front face adapted to face the air gap, a back face adapted to face away from the air gap, and a side face generally connecting said front and back faces; and shielding cap means connected to said magnet means for focusing the magnetic energy of said magnet means, said shielding cap means formed of material having a high relative magnetic permeability and having a size and shape to substantially conform to the size and shape of said back face of said magnet means.

10. The hearing aid of claim 9, wherein said shielding cap means is further located adjacent the side face of said magnet means and has a size and shape to substantially conform to part of the thickness of said side face of said magnet means.

11. The hearing aid of claim 9, wherein said magnet means front and back faces have an area substantially greater than the area of said side face and thus develop a central axis from the center of said front face to the center of said back face and said magnet means and said shielding cap means have a thickness varying with the distance form the central axis of the magnet means.

12. The hearing aid of claim 11, wherein said shielding cap means is located adjacent said side face of said magnet means and has a size and shape to substantially conform to part of the thickness of said side face of said magnet means.

13. A middle ear ossicular replacement prosthesis for replacing at least a portion of the ossicular chain by making contact with two separate locations in the middle ear and for use with a hearing aid having a coil for producing a magnetic field corresponding to sound waves received by the wearer, comprising:

a head portion adapted to contact the tympanic membrane, said head portion including a magnet assembly; and a shaft portion extending from said head portion to a location in the middle ear, wherein said head portion and said shaft portion are adapted to transmit to the inner ear the acoustically induced vibrations of the tympanic membrane received by said head portion and the magnetically induced vibrations developed by the coupling of the magnetic field produced by said magnet assembly and the magnetic field produced by the hearing aid, and wherein said magnet assembly comprises:

magnet means adapted to be spaced a fixed distance form the coil for forming an air gap, said magnet means including a front face adapted to face the air gap, a back face adapted to face away from the air gap, and a side face generally connecting said front and back faces; and shielding cap means connected to said magnet means for focusing the magnetic energy and said magnet means, said shielding cap means formed of material having a high relative magnetic permeability and having a size and shape to substantially conform to the size and shape of said back face of said magnet means.

14. The prosthesis of claim 13, wherein said shielding cap means is further located adjacent the side face of said magnet means and has a size and shape to substantially conform to part of the thickness of said side face of said magnet means.

15. The prosthesis of claim 13, wherein said magnet means front and back faces have an area substantially greater than the area of said side face and thus develop a central axis from the center of said front face to the center of said back face and said magnet means and said shielding cap means have a thickness varying with the distance form the central axis of the magnet means.

16. The prosthesis of claim 15, wherein said shielding cap means is located adjacent said side face of said magnet means and has a size and shape to substantially conform to part of the thickness of said side face of said magnet means.

* * * * *

UNITED STATES PATENT AND TRADEMARK OFFICE
CERTIFICATE OF CORRECTION

PATENT NO. : 4,936,305

DATED : June 26, 1990

INVENTOR(S) : Ashtiani et al.

It is certified that error appears in the above-identified patent and that said Letters Patent is hereby corrected as shown below:

At column 4, line 21, delete "S" and insert --$S_1$--.

At column 4, line 47, delete "S" and insert --$S_1$--.

At column 6, line 6, delete "TEST 1" and insert --TEST 3--.

At column 7, line 63, delete "P" and insert --$P_1$--.

Signed and Sealed this

Seventeenth Day of December, 1991

*Attest:*

HARRY F. MANBECK, JR.

*Attesting Officer* *Commissioner of Patents and Trademarks*